United States Patent
Doron

(10) Patent No.: US 8,591,423 B2
(45) Date of Patent: Nov. 26, 2013

(54) SYSTEMS AND METHODS FOR DETERMINING CARDIAC OUTPUT USING PULMONARY ARTERY PRESSURE MEASUREMENTS

(75) Inventor: Eyal Doron, Kiriat-Yam (IL)

(73) Assignee: Cardiac Pacemakers, Inc., St. Paul, MN (US)

( * ) Notice: Subject to any disclaimer, the term of this patent is extended or adjusted under 35 U.S.C. 154(b) by 415 days.

(21) Appl. No.: 12/557,384

(22) Filed: Sep. 10, 2009

(65) Prior Publication Data

US 2010/0094144 A1 Apr. 15, 2010

Related U.S. Application Data

(60) Provisional application No. 61/104,405, filed on Oct. 10, 2008.

(51) Int. Cl.
*A61B 5/0215* (2006.01)

(52) U.S. Cl.
USPC .................. 600/486; 600/485; 600/481

(58) Field of Classification Search
USPC .................................. 600/485, 486
See application file for complete search history.

(56) References Cited

U.S. PATENT DOCUMENTS

| | | | |
|---|---|---|---|
| 3,310,885 A | 3/1967 | Alderson |
| 3,320,946 A | 5/1967 | Dethloff et al. |
| 3,536,836 A | 10/1970 | Pfeiffer |
| 3,568,661 A | 3/1971 | Franklin |
| 3,672,352 A | 6/1972 | Summers |
| 3,692,027 A | 9/1972 | Ellinwood |
| 3,757,770 A | 9/1973 | Brayshaw et al. |
| 3,794,840 A | 2/1974 | Scott |
| 3,943,915 A | 3/1976 | Severson |
| 4,003,379 A | 1/1977 | Ellinwood |
| 4,041,954 A | 8/1977 | Ohara |
| 4,127,110 A | 11/1978 | Bullara |
| 4,146,029 A | 3/1979 | Ellinwood |
| 4,223,801 A | 9/1980 | Carlson |
| 4,227,407 A | 10/1980 | Drost |
| 4,237,900 A | 12/1980 | Schulman et al. |
| 4,281,664 A | 8/1981 | Duggen |

(Continued)

FOREIGN PATENT DOCUMENTS

| | | |
|---|---|---|
| EP | 0 897 690 | 2/1999 |
| EP | 0 928 598 | 7/1999 |

(Continued)

OTHER PUBLICATIONS

"Controversy Over the Dicrotic Notch and Wave in the Blood Pressure Record". Geddes et al. Engineering in Medicine and Biology Magazine, IEEE. vol. 21, Issue 5. pp. 167-169. 2002.*

(Continued)

*Primary Examiner* — Navin Natnithithadha
*Assistant Examiner* — Meredith Weare
(74) *Attorney, Agent, or Firm* — Faegre Baker Daniels LLP

(57) ABSTRACT

Systems and methods for determining cardiac output are disclosed. An illustrative method of determining cardiac output includes sensing an arterial pressure waveform using a pressure sensor located within a pulmonary artery, identifying a valve closure time associated with the pulmonary valve using the sensed arterial pressure waveform, estimating stroke volume using the systolic portion of the arterial pressure waveform and the valve closure time, and obtaining a measure of cardiac output based on the estimated stroke volume.

18 Claims, 4 Drawing Sheets

(56) References Cited

U.S. PATENT DOCUMENTS

| | | |
|---|---|---|
| 4,360,019 A | 11/1982 | Portner et al. |
| 4,407,296 A | 10/1983 | Anderson |
| 4,450,527 A | 5/1984 | Sramek |
| 4,480,483 A | 11/1984 | McShane |
| 4,519,401 A | 5/1985 | Ko et al. |
| 4,541,431 A | 9/1985 | Ibrahim et al. |
| 4,543,955 A | 10/1985 | Schroeppel |
| 4,550,370 A | 10/1985 | Baker |
| 4,585,004 A | 4/1986 | Brownlee |
| 4,593,703 A | 6/1986 | Cosman |
| 4,600,855 A | 7/1986 | Strachan |
| 4,616,640 A | 10/1986 | Kaali et al. |
| 4,651,740 A | 3/1987 | Schroeppel |
| 4,653,508 A | 3/1987 | Cosman |
| 4,660,568 A | 4/1987 | Cosman |
| 4,676,255 A | 6/1987 | Cosman |
| 4,677,985 A | 7/1987 | Bro et al. |
| 4,680,957 A | 7/1987 | Dodd |
| 4,686,987 A | 8/1987 | Salo et al. |
| 4,697,595 A | 10/1987 | Breyer et al. |
| 4,719,921 A | 1/1988 | Chirife |
| 4,768,176 A | 8/1988 | Kehr et al. |
| 4,768,177 A | 8/1988 | Kehr et al. |
| 4,781,715 A | 11/1988 | Wurzel |
| 4,791,936 A | 12/1988 | Snell et al. |
| 4,793,825 A | 12/1988 | Lochow et al. |
| 4,809,697 A | 3/1989 | Causey, III et al. |
| 4,845,503 A | 7/1989 | Adam et al. |
| 4,846,191 A | 7/1989 | Brockway et al. |
| 4,854,327 A | 8/1989 | Kunig |
| 4,899,752 A | 2/1990 | Cohen |
| 4,909,259 A | 3/1990 | Tehrani |
| 4,945,914 A | 8/1990 | Allen |
| 4,967,749 A | 11/1990 | Cohen |
| 4,986,270 A | 1/1991 | Cohen |
| 4,991,579 A | 2/1991 | Allen |
| 4,995,068 A | 2/1991 | Chou et al. |
| 4,995,398 A | 2/1991 | Turnidge |
| 5,003,976 A | 4/1991 | Alt |
| 5,024,224 A | 6/1991 | Engebretson |
| 5,025,795 A | 6/1991 | Kunig |
| 5,029,582 A | 7/1991 | Lekholm |
| 5,040,536 A | 8/1991 | Riff |
| 5,040,538 A | 8/1991 | Mortazavi |
| 5,113,859 A | 5/1992 | Funke |
| 5,139,020 A | 8/1992 | Koestner et al. |
| 5,154,171 A | 10/1992 | Chirife |
| 5,161,536 A | 11/1992 | Vilkomerson et al. |
| 5,163,429 A | 11/1992 | Cohen |
| 5,178,151 A | 1/1993 | Sackner |
| 5,178,153 A | 1/1993 | Einzig |
| 5,183,051 A * | 2/1993 | Kraidin et al. ................ 600/500 |
| 5,188,106 A | 2/1993 | Nappholz et al. |
| 5,190,035 A | 3/1993 | Salo et al. |
| 5,199,428 A | 4/1993 | Obel et al. |
| 5,200,891 A | 4/1993 | Kehr et al. |
| 5,213,098 A | 5/1993 | Bennett et al. |
| 5,246,008 A | 9/1993 | Mueller |
| 5,265,615 A | 11/1993 | Frank et al. |
| 5,267,174 A | 11/1993 | Kaufman et al. |
| 5,277,191 A | 1/1994 | Hughes |
| 5,279,309 A | 1/1994 | Taylor et al. |
| 5,279,607 A | 1/1994 | Schentag et al. |
| 5,289,821 A | 3/1994 | Swartz |
| 5,300,092 A | 4/1994 | Schaldach |
| 5,314,457 A | 5/1994 | Jeutter et al. |
| 5,329,459 A | 7/1994 | Kaufman et al. |
| 5,330,505 A | 7/1994 | Cohen |
| 5,339,051 A | 8/1994 | Koehler et al. |
| 5,368,040 A | 11/1994 | Carney |
| 5,375,603 A | 12/1994 | Feiler |
| 5,394,457 A | 2/1995 | Leibinger et al. |
| 5,397,329 A | 3/1995 | Allen |
| 5,400,793 A | 3/1995 | Wesseling |
| 5,411,535 A | 5/1995 | Fujii et al. |
| 5,411,551 A | 5/1995 | Winston et al. |
| 5,417,717 A | 5/1995 | Salo et al. |
| 5,423,323 A | 6/1995 | Orth |
| 5,423,334 A | 6/1995 | Jordan |
| 5,438,990 A | 8/1995 | Wahlstrand et al. |
| 5,445,608 A | 8/1995 | Chen et al. |
| 5,454,838 A | 10/1995 | Vallana et al. |
| 5,469,859 A | 11/1995 | Tsoglin et al. |
| 5,476,488 A | 12/1995 | Morgan et al. |
| 5,488,954 A | 2/1996 | Sleva et al. |
| 5,490,962 A | 2/1996 | Cima et al. |
| 5,509,424 A | 4/1996 | Al Ali |
| 5,528,067 A | 6/1996 | Farb |
| 5,535,752 A | 7/1996 | Halperin et al. |
| 5,558,091 A | 9/1996 | Acker et al. |
| 5,562,714 A | 10/1996 | Grevious |
| 5,564,434 A | 10/1996 | Halperin et al. |
| 5,571,152 A | 11/1996 | Chen et al. |
| 5,604,531 A | 2/1997 | Iddan et al. |
| 5,605,154 A | 2/1997 | Ries et al. |
| 5,619,997 A | 4/1997 | Kaplan |
| 5,626,630 A | 5/1997 | Markowitz et al. |
| 5,628,782 A | 5/1997 | Myers |
| 5,642,731 A | 7/1997 | Kehr |
| 5,643,327 A | 7/1997 | Dawson et al. |
| 5,647,369 A | 7/1997 | Petrucelli et al. |
| 5,656,428 A | 8/1997 | McAllister et al. |
| 5,704,352 A | 1/1998 | Tremblay et al. |
| 5,705,753 A | 1/1998 | Hastings et al. |
| 5,728,281 A | 3/1998 | Holmstrom et al. |
| 5,729,129 A | 3/1998 | Acker |
| 5,733,313 A | 3/1998 | Barreras, Sr. et al. |
| 5,735,887 A | 4/1998 | Barreras, Sr. et al. |
| 5,741,316 A | 4/1998 | Chen et al. |
| 5,749,909 A | 5/1998 | Schroeppel et al. |
| 5,752,235 A | 5/1998 | Kehr et al. |
| 5,752,976 A | 5/1998 | Duffin et al. |
| 5,755,766 A | 5/1998 | Chastain et al. |
| 5,769,877 A | 6/1998 | Barreras, Sr. |
| 5,776,324 A | 7/1998 | Usala |
| 5,792,195 A | 8/1998 | Carlson et al. |
| 5,796,827 A | 8/1998 | Coppersmith et al. |
| 5,797,395 A | 8/1998 | Martin |
| 5,800,478 A | 9/1998 | Chen et al. |
| 5,807,258 A | 9/1998 | Cimochowski et al. |
| 5,807,395 A | 9/1998 | Mulier et al. |
| 5,807,397 A | 9/1998 | Barreras |
| 5,810,009 A | 9/1998 | Mine et al. |
| 5,810,735 A | 9/1998 | Halperin et al. |
| 5,832,924 A | 11/1998 | Archibald et al. |
| 5,833,603 A | 11/1998 | Kovacs et al. |
| 5,835,455 A | 11/1998 | Hanson et al. |
| 5,836,300 A | 11/1998 | Mault |
| 5,843,135 A | 12/1998 | Weijand et al. |
| 5,855,609 A | 1/1999 | Knapp |
| 5,856,722 A | 1/1999 | Haronian et al. |
| 5,868,673 A | 2/1999 | Vesely |
| 5,873,835 A | 2/1999 | Hastings et al. |
| 5,886,267 A | 3/1999 | Ortiz |
| 5,891,180 A | 4/1999 | Greeninger et al. |
| 5,904,708 A | 5/1999 | Goedeke et al. |
| 5,911,685 A | 6/1999 | Siess et al. |
| 5,919,221 A | 7/1999 | Miesel |
| 5,941,249 A | 8/1999 | Maynard |
| 5,954,641 A | 9/1999 | Kehr et al. |
| 5,957,950 A | 9/1999 | Mockros et al. |
| 5,967,986 A | 10/1999 | Cimochowski et al. |
| 5,979,898 A | 11/1999 | Pan |
| 6,002,963 A | 12/1999 | Mouchawar et al. |
| 6,023,641 A | 2/2000 | Thompson |
| 6,024,704 A | 2/2000 | Meador et al. |
| 6,050,951 A | 4/2000 | Friedman et al. |
| 6,053,873 A | 4/2000 | Govari et al. |
| 6,083,248 A | 7/2000 | Thompson |
| 6,112,116 A | 8/2000 | Fischell et al. |
| 6,123,861 A | 9/2000 | Santini, Jr. et al. |
| 6,140,740 A | 10/2000 | Porat et al. |
| 6,141,588 A | 10/2000 | Cox et al. |
| 6,152,885 A | 11/2000 | Taepke |

(56) References Cited

U.S. PATENT DOCUMENTS

| | | | |
|---|---|---|---|
| 6,155,267 A | 12/2000 | Nelson | |
| 6,161,032 A | 12/2000 | Acker | |
| 6,162,238 A | 12/2000 | Kaplan et al. | |
| 6,171,252 B1 | 1/2001 | Roberts | |
| 6,179,767 B1 | 1/2001 | Ziegler et al. | |
| 6,185,452 B1 | 2/2001 | Shulman et al. | |
| 6,198,965 B1 | 3/2001 | Penner et al. | |
| 6,200,265 B1 | 3/2001 | Walsh et al. | |
| 6,234,973 B1 | 5/2001 | Meador et al. | |
| 6,236,889 B1 | 5/2001 | Soykan et al. | |
| 6,237,398 B1 | 5/2001 | Porat et al. | |
| 6,239,724 B1 | 5/2001 | Doron et al. | |
| 6,248,080 B1 | 6/2001 | Miesel et al. | |
| 6,256,538 B1 | 7/2001 | Ekwall | |
| 6,266,567 B1 | 7/2001 | Ishikawa et al. | |
| 6,273,904 B1 | 8/2001 | Chen et al. | |
| 6,277,078 B1 | 8/2001 | Porat et al. | |
| 6,278,894 B1 | 8/2001 | Salo et al. | |
| 6,298,267 B1 | 10/2001 | Rosborough et al. | |
| 6,305,381 B1 | 10/2001 | Weijand et al. | |
| 6,308,099 B1 | 10/2001 | Fox et al. | |
| 6,314,323 B1* | 11/2001 | Ekwall | 607/23 |
| 6,330,957 B1 | 12/2001 | Bell-Greenstreet | |
| 6,331,163 B1 | 12/2001 | Kaplan | |
| 6,368,275 B1 | 4/2002 | Sliwa et al. | |
| 6,394,958 B1* | 5/2002 | Bratteli et al. | 600/485 |
| 6,397,661 B1 | 6/2002 | Grimes et al. | |
| 6,409,674 B1 | 6/2002 | Brockway et al. | |
| 6,409,675 B1 | 6/2002 | Turcott | |
| 6,411,850 B1 | 6/2002 | Kay et al. | |
| 6,416,474 B1 | 7/2002 | Penner et al. | |
| 6,421,565 B1 | 7/2002 | Hemmingsson | |
| 6,431,175 B1 | 8/2002 | Penner et al. | |
| 6,432,050 B1 | 8/2002 | Porat et al. | |
| 6,438,408 B1 | 8/2002 | Mulligan et al. | |
| 6,441,747 B1 | 8/2002 | Khair et al. | |
| 6,442,413 B1 | 8/2002 | Silver | |
| 6,445,953 B1 | 9/2002 | Bulkes et al. | |
| 6,456,883 B1 | 9/2002 | Torgerson et al. | |
| 6,471,645 B1 | 10/2002 | Warkentin et al. | |
| 6,472,991 B1 | 10/2002 | Schulman et al. | |
| 6,475,147 B1 | 11/2002 | Yost et al. | |
| 6,475,170 B1 | 11/2002 | Doron et al. | |
| 6,486,588 B2 | 11/2002 | Doron et al. | |
| 6,504,286 B1 | 1/2003 | Porat et al. | |
| 6,522,914 B1 | 2/2003 | Huvelle et al. | |
| 6,567,700 B1 | 5/2003 | Turcott et al. | |
| 6,574,510 B2 | 6/2003 | Von Arx et al. | |
| 6,580,946 B2 | 6/2003 | Struble | |
| 6,604,000 B2 | 8/2003 | Lu | |
| 6,607,485 B2 | 8/2003 | Bardy | |
| 6,609,023 B1 | 8/2003 | Fischell et al. | |
| 6,615,083 B2 | 9/2003 | Kupper | |
| 6,622,049 B2 | 9/2003 | Penner et al. | |
| 6,628,989 B1 | 9/2003 | Penner et al. | |
| 6,638,231 B2 | 10/2003 | Govari et al. | |
| 6,644,322 B2 | 11/2003 | Webb | |
| 6,654,638 B1 | 11/2003 | Sweeney | |
| 6,675,049 B2 | 1/2004 | Thompson et al. | |
| 6,699,186 B1 | 3/2004 | Wolinsky et al. | |
| 6,702,847 B2 | 3/2004 | DiCarlo | |
| 6,708,061 B2 | 3/2004 | Salo et al. | |
| 6,708,065 B2 | 3/2004 | Von Arx et al. | |
| 6,712,772 B2 | 3/2004 | Cohen et al. | |
| 6,720,709 B2 | 4/2004 | Porat et al. | |
| 6,720,887 B1 | 4/2004 | Zunti | |
| 6,733,447 B2 | 5/2004 | Lai et al. | |
| 6,738,667 B2 | 5/2004 | Deno et al. | |
| 6,738,671 B2 | 5/2004 | Christophersom et al. | |
| 6,743,173 B2 | 6/2004 | Penner et al. | |
| 6,758,822 B2* | 7/2004 | Romano | 600/526 |
| 6,764,446 B2 | 7/2004 | Wolinsky et al. | |
| 6,782,810 B2 | 8/2004 | Vilo | |
| 6,783,499 B2 | 8/2004 | Schwartz | |
| 6,792,308 B2 | 9/2004 | Corbucci | |
| 6,792,311 B2 | 9/2004 | Fox et al. | |
| 6,805,667 B2 | 10/2004 | Christopherson et al. | |
| 6,809,507 B2 | 10/2004 | Morgan et al. | |
| 6,824,512 B2 | 11/2004 | Warkentin et al. | |
| 6,832,112 B1 | 12/2004 | Bornzin | |
| 6,840,956 B1 | 1/2005 | Wolinsky et al. | |
| 6,855,115 B2 | 2/2005 | Fonseca et al. | |
| 6,859,665 B2 | 2/2005 | Ding et al. | |
| 6,865,419 B2 | 3/2005 | Mulligan et al. | |
| 6,868,346 B2 | 3/2005 | Larson et al. | |
| 6,869,404 B2 | 3/2005 | Schulhauser et al. | |
| 6,871,088 B2 | 3/2005 | Chinchoy | |
| 6,885,889 B2 | 4/2005 | Chinchoy | |
| 6,889,086 B2 | 5/2005 | Mass et al. | |
| 6,895,265 B2 | 5/2005 | Silver | |
| 6,907,285 B2 | 6/2005 | Denker et al. | |
| 6,915,162 B2 | 7/2005 | Noren et al. | |
| 6,926,670 B2 | 8/2005 | Rich et al. | |
| 6,937,900 B1 | 8/2005 | Pianca et al. | |
| 6,949,075 B2 | 9/2005 | Hatlestad et al. | |
| 6,961,448 B2 | 11/2005 | Nichols et al. | |
| 6,970,742 B2 | 11/2005 | Mann et al. | |
| 6,978,182 B2 | 12/2005 | Mazar et al. | |
| 6,985,773 B2 | 1/2006 | Von Arx et al. | |
| 6,993,393 B2 | 1/2006 | Von Arx et al. | |
| 7,003,350 B2 | 2/2006 | Denker et al. | |
| 7,018,336 B2 | 3/2006 | Enegren et al. | |
| 7,024,248 B2 | 4/2006 | Penner et al. | |
| 7,033,322 B2 | 4/2006 | Silver | |
| 7,035,684 B2 | 4/2006 | Lee | |
| 7,047,065 B2 | 5/2006 | Kalgren et al. | |
| 7,048,691 B2 | 5/2006 | Miele et al. | |
| 7,060,030 B2 | 6/2006 | Von Arx et al. | |
| 7,061,381 B2 | 6/2006 | Forcier et al. | |
| 7,088,254 B2 | 8/2006 | Liebenow | |
| 7,090,648 B2* | 8/2006 | Sackner et al. | 601/1 |
| 7,127,290 B2 | 10/2006 | Girouard et al. | |
| 7,130,681 B2 | 10/2006 | Gebhardt et al. | |
| 7,134,999 B2 | 11/2006 | Brauker et al. | |
| 7,136,703 B1 | 11/2006 | Cappa et al. | |
| 7,160,252 B2 | 1/2007 | Cho et al. | |
| 7,181,268 B2 | 2/2007 | Sheldon et al. | |
| 7,195,594 B2 | 3/2007 | Eigler et al. | |
| 7,198,603 B2 | 4/2007 | Penner et al. | |
| 7,200,439 B2 | 4/2007 | Zdeblick et al. | |
| 7,203,545 B2 | 4/2007 | Schmitt et al. | |
| 7,204,798 B2 | 4/2007 | Zdeblick et al. | |
| 7,209,790 B2 | 4/2007 | Thompson et al. | |
| 7,212,861 B1 | 5/2007 | Park et al | |
| 7,214,189 B2 | 5/2007 | Zdeblick | |
| 7,236,821 B2 | 6/2007 | Cates et al. | |
| 7,248,923 B2 | 7/2007 | Maile et al. | |
| 7,273,457 B2 | 9/2007 | Penner | |
| 7,294,105 B1 | 11/2007 | Islam | |
| 7,335,161 B2 | 2/2008 | Von Arx et al. | |
| 7,399,313 B2 | 7/2008 | Brown et al. | |
| 7,425,200 B2 | 9/2008 | Brockway et al. | |
| 7,452,334 B2 | 11/2008 | Gianchandani et al. | |
| 7,481,771 B2 | 1/2009 | Fonseca et al. | |
| 7,742,815 B2 | 6/2010 | Salo et al. | |
| 2001/0051766 A1 | 12/2001 | Gazdzinski | |
| 2001/0051787 A1 | 12/2001 | Haller et al. | |
| 2002/0022785 A1* | 2/2002 | Romano | 600/526 |
| 2002/0023123 A1 | 2/2002 | Madison | |
| 2002/0042561 A1 | 4/2002 | Schulman et al. | |
| 2002/0045812 A1 | 4/2002 | Ben-Haim et al. | |
| 2002/0045836 A1 | 4/2002 | Alkawwas | |
| 2002/0045921 A1* | 4/2002 | Wolinsky et al. | 607/61 |
| 2002/0062086 A1 | 5/2002 | Miele et al. | |
| 2002/0103454 A1* | 8/2002 | Sackner et al. | 604/19 |
| 2002/0120204 A1* | 8/2002 | Pfeiffer et al. | 600/505 |
| 2002/0126036 A1 | 9/2002 | Flaherty et al. | |
| 2002/0147406 A1 | 10/2002 | von Segesser | |
| 2002/0151770 A1 | 10/2002 | Noll, III et al. | |
| 2002/0183628 A1 | 12/2002 | Reich et al. | |
| 2002/0188323 A1 | 12/2002 | Penner et al. | |
| 2003/0009204 A1 | 1/2003 | Amundson et al. | |
| 2003/0023173 A1* | 1/2003 | Bratteli et al. | 600/485 |
| 2003/0045805 A1 | 3/2003 | Sheldon et al. | |

(56) References Cited

U.S. PATENT DOCUMENTS

| | | |
|---|---|---|
| 2003/0060723 A1 | 3/2003 | Joo et al. |
| 2003/0114897 A1 | 6/2003 | Von Arx et al. |
| 2003/0136417 A1 | 7/2003 | Fonseca et al. |
| 2003/0181794 A1 | 9/2003 | Rini et al. |
| 2003/0191383 A1 | 10/2003 | Ben-Haim et al. |
| 2003/0199779 A1* | 10/2003 | Muhlenberg et al. ......... 600/513 |
| 2004/0032187 A1 | 2/2004 | Penner et al. |
| 2004/0044393 A1 | 3/2004 | Yarden et al. |
| 2004/0064133 A1 | 4/2004 | Miller et al. |
| 2004/0077937 A1 | 4/2004 | Yarden |
| 2004/0122484 A1 | 6/2004 | Hatlestad et al. |
| 2004/0122486 A1 | 6/2004 | Stahmann et al. |
| 2004/0152999 A1 | 8/2004 | Cohen et al. |
| 2004/0158163 A1 | 8/2004 | Cohen et al. |
| 2004/0167416 A1 | 8/2004 | Lee |
| 2004/0172081 A1 | 9/2004 | Wang |
| 2005/0056539 A1 | 3/2005 | Morgan et al. |
| 2005/0102002 A1 | 5/2005 | Salo et al. |
| 2005/0109339 A1* | 5/2005 | Stahmann et al. ....... 128/204.18 |
| 2005/0124904 A1 | 6/2005 | Roteliuk |
| 2005/0137490 A1 | 6/2005 | Scheiner et al. |
| 2005/0149143 A1 | 7/2005 | Libbus et al. |
| 2005/0154321 A1 | 7/2005 | Wolinsky et al. |
| 2005/0159639 A1 | 7/2005 | Skliar et al. |
| 2005/0159789 A1 | 7/2005 | Brockway et al. |
| 2005/0182330 A1 | 8/2005 | Brockway et al. |
| 2005/0187482 A1 | 8/2005 | O'Brien et al. |
| 2005/0192637 A1 | 9/2005 | Girouard et al. |
| 2005/0192844 A1 | 9/2005 | Esler et al. |
| 2005/0197585 A1 | 9/2005 | Brockway et al. |
| 2005/0215887 A1 | 9/2005 | Ben-Haim et al. |
| 2005/0242479 A1 | 11/2005 | Petisce et al. |
| 2005/0265999 A1 | 12/2005 | Bush et al. |
| 2005/0267379 A1* | 12/2005 | Pfeiffer et al. ................ 600/526 |
| 2005/0288727 A1 | 12/2005 | Penner |
| 2006/0009818 A1 | 1/2006 | Von Arx et al. |
| 2006/0031378 A1 | 2/2006 | Vallapureddy et al. |
| 2006/0064133 A1 | 3/2006 | Von Arx et al. |
| 2006/0064134 A1 | 3/2006 | Mazar et al. |
| 2006/0064142 A1 | 3/2006 | Chavan et al. |
| 2006/0064143 A1 | 3/2006 | Von Arx et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0089694 A1 | 4/2006 | Zhang et al. |
| 2006/0122522 A1 | 6/2006 | Chavan et al. |
| 2006/0136004 A1 | 6/2006 | Cowan et al. |
| 2006/0142651 A1 | 6/2006 | Brister et al. |
| 2006/0167359 A1 | 7/2006 | Bennett et al. |
| 2006/0167361 A1* | 7/2006 | Bennett et al. ................ 600/486 |
| 2006/0235323 A1* | 10/2006 | Hatib et al. .................... 600/526 |
| 2007/0043394 A1 | 2/2007 | Zhang et al. |
| 2007/0049977 A1 | 3/2007 | Von Arx et al. |
| 2007/0060959 A1 | 3/2007 | Salo et al. |
| 2007/0088221 A1* | 4/2007 | Stahmann ..................... 600/485 |
| 2007/0129765 A1 | 6/2007 | Gilkerson et al. |
| 2007/0142727 A1 | 6/2007 | Zhang et al. |
| 2007/0142866 A1 | 6/2007 | Li et al. |
| 2007/0149890 A1 | 6/2007 | Li et al. |
| 2007/0161914 A1 | 7/2007 | Zdeblick et al. |
| 2007/0197921 A1* | 8/2007 | Cohen et al. .................. 600/485 |
| 2007/0282210 A1* | 12/2007 | Stern ............................. 600/486 |
| 2007/0282381 A1 | 12/2007 | Li et al. |
| 2008/0015421 A1 | 1/2008 | Penner |
| 2008/0015651 A1 | 1/2008 | Ettori et al. |
| 2008/0021333 A1 | 1/2008 | Huelskamp |
| 2008/0021972 A1 | 1/2008 | Huelskamp et al. |
| 2008/0046037 A1 | 2/2008 | Haubrich et al. |
| 2008/0051843 A1 | 2/2008 | Li et al. |
| 2008/0071178 A1 | 3/2008 | Greenland et al. |
| 2008/0077440 A1 | 3/2008 | Doron |
| 2008/0243007 A1 | 10/2008 | Liao et al. |
| 2009/0201148 A1 | 8/2009 | Tran et al. |
| 2009/0204163 A1 | 8/2009 | Shuros et al. |
| 2009/0228078 A1 | 9/2009 | Zhang et al. |
| 2010/0056931 A1* | 3/2010 | Soffer et al. .................. 600/486 |
| 2010/0125211 A1 | 5/2010 | Stahmann et al. |
| 2010/0222833 A1 | 9/2010 | Salo et al. |
| 2010/0324378 A1 | 12/2010 | Tran et al. |

FOREIGN PATENT DOCUMENTS

| | | |
|---|---|---|
| EP | 1 266 606 | 12/2002 |
| EP | 1 169 085 | 8/2004 |
| JP | 03-034196 | 2/1991 |
| JP | 10-055202 | 2/1998 |
| JP | 2004528152 | 9/2004 |
| JP | 2006-523120 | 10/2006 |
| JP | 2007-516796 A | 6/2007 |
| JP | 2007-519441 | 7/2007 |
| WO | WO83/03345 | 10/1983 |
| WO | WO95/03086 | 2/1995 |
| WO | WO95/27531 | 10/1995 |
| WO | WO97/01986 | 1/1997 |
| WO | WO 97/18856 | 5/1997 |
| WO | WO97/32519 | 9/1997 |
| WO | WO97/33513 | 9/1997 |
| WO | WO97/47236 | 12/1997 |
| WO | WO98/26716 | 6/1998 |
| WO | WO98/29030 | 7/1998 |
| WO | WO99/17095 | 4/1999 |
| WO | WO99/26530 | 6/1999 |
| WO | WO99/34453 | 7/1999 |
| WO | WO99/47205 | 9/1999 |
| WO | WO99/55223 | 11/1999 |
| WO | WO99/55225 | 11/1999 |
| WO | WO99/59460 | 11/1999 |
| WO | WO99/66988 | 12/1999 |
| WO | WO00/16686 | 3/2000 |
| WO | WO00/58744 | 10/2000 |
| WO | WO01/28627 | 4/2001 |
| WO | WO01/56467 | 8/2001 |
| WO | WO01/74278 | 10/2001 |
| WO | WO 01/76687 | 10/2001 |
| WO | WO 01/85094 | 11/2001 |
| WO | WO02/03347 | 1/2002 |
| WO | WO02/32502 | 4/2002 |
| WO | WO03/002243 | 1/2003 |
| WO | WO03/096889 | 11/2003 |
| WO | WO2004012808 | 2/2004 |
| WO | WO 2004/091719 | 10/2004 |
| WO | WO2005000206 | 1/2005 |
| WO | WO 2005/065771 A1 | 7/2005 |
| WO | WO2005063332 A1 | 7/2005 |
| WO | WO2005/089638 | 9/2005 |
| WO | WO2005/118056 | 12/2005 |
| WO | WO2006/033812 | 3/2006 |
| WO | WO2006/034183 | 3/2006 |
| WO | WO2006/045073 | 4/2006 |
| WO | WO2006/045074 | 4/2006 |
| WO | WO2006/045075 | 4/2006 |
| WO | WO2006/069215 | 6/2006 |
| WO | WO 2006/124833 | 11/2006 |
| WO | WO2007/030474 | 3/2007 |
| WO | WO2007/047287 | 4/2007 |
| WO | WO2007/070794 | 6/2007 |
| WO | WO2007/099533 | 9/2007 |
| WO | WO2008/011570 | 1/2008 |
| WO | WO2008/011592 | 1/2008 |
| WO | WO2008/011593 | 1/2008 |
| WO | WO2008/154145 | 12/2008 |

OTHER PUBLICATIONS

"Correlation of Mean Pulmonary Artery Wedge Pressure, Left Atrial Dimension, and PTF-V1 in Patients with Acute Myocardial Infarction" Orlando et al. Circulation 1977, 55:750-752.*

"Evaluation of Pulse Contour Methods in Calculating Stroke Volume from Pulmonary Artery Pressure Curve". Tajimi et al. European Heart Journal, vol. 4, Issue7, pp. 502-511. 1983.*

Zacharoulis et al. "Measurement of stroke volume from pulmonary artery pressure record in man." British Heart Journal, 1975, 37, 20-25.*

(56) References Cited

OTHER PUBLICATIONS

Humphrey et al. "An analysis of direct and indirect measurements of left atrial filling pressure." Thoracic and Cardiovascular Surgery, May 1976, 71(5), 643-647.*
"Pulmonary valve." http://en.wikipedia.org/wiki/Pulmonary_valve.*
"Cardiac output." http://en.wikipedia.org/wiki/Cardiac_output.*
Takazawa et al. "Assessment of Vasoactive Agents and Vascular Aging by the Second Derivative of Photoplethysmogram Waveform." Hypertension. 1998;32:365-370.*
B. C. Penney et al., "Simplified electrode array for impedance cardiography," Medical & Biological Engineering & Computing, 1985, 23, p. 1-7.
B. Henderson et al., "Interaction of Photodynamic Therapy and Hyperthermia: Tumor Response and Cell Survival after Treatment of Mice in Vivo," Cancer Research, vol. 45, 6071 (Dec. 1985).
Bennett et al., "Subcutaneous pressure measurement as a surrogate for an external pressure reference for chronic implantable pressure monitoring," Journal of Cardial Failure, Churchill Livingstone, vol. 9, No. 5, p. S51, Oct. 1, 2003, abstract only.
Bonnefoy E, Ninet J, Robin J, Leroux F, Boissonat P, Brule P, Champsaur G., 1994, Bipolar intramyocardial electrogram from an implanted telemetric pacemaker for the diagnosis of cardiac allograft rejection, Pacing Clin Electrophysiol, 17(11 Pt 2):2052-6.
Bourgeois, Maurice J. et al., "Continuous Determination of Beat-to-Beat Stroke Volume from Aortic pressure Pulses in the Dog", Circulation Research, vol. 39, pp. 15-24 (1976).
C. Hierold et al. (Germany, 1998) "Implantable Low Power Integrated Pressure Sensor System for Minimal Invasive Telemetric Patient Monitoring" IEEE, pp. 568-573.
Dipl.-Ing. Torsten Eggers et al. (Germany) "Implantable Telemetric Endosytem (ITES)" IMSAS Institut Fur Mikrosensoren-Aktuatoren Und-Systeme, 1998. 2 pp.
E R. Cosman et al. (Massachussetts, Apr. 1979) "A Telemetric Pressure Sensor for Ventricular Shunt Systems" Surgical Neurology vol. 11, No. 4, pp. 287-294.
Fink, Mathias, "Time Reversal of Ultrasonic Fields—Part I: Basic Principles", IEEE Transactions on Ultrasonics, Ferroelectrics, and Frequency Control, vol. 39, No. 5, Sep. 1992, pp. 555-566.
G.W.H. Schurink et al. (1998) "Late Endoleak After Endovascular Therapy for Abdominal Aortic Aneurysm" Eur. J. Vasc. Endovasc. Surg. vol. 17, pp. 448-450.
Gerhausser A, Reichel T, Neukomm P A, Bolz A, Hugel J, Schaldach M, 1997, Diagnosis of rejection after kidney transplantation by impedance spectroscopy with an implantable measuring system, Biomed Tech (Berl), 42 Suppl. 160-1.
GH White et al. (1997) "Endoleak Following Endoluminal Repair of AAA: Management Options and Patient Outcomes", J. Endovasc Surg, pp. 1-45.
Graichen et al., "Patient Monitoring System for Load Measurement with Spinal Fixation Devices," Med. Eng. Phys. 18, (1996), pp. 167-174.
Haas et al., "Photodynamic Effects of Dyes on Bacteria," Published in Mutation Research, 1979, vol. 60, pp. 1-11.
Hashima et al., "Nonhomogenous Analysis of Epicardial Strain Distributions During Acute Myocardial Ischemia in the Dog," J Biomech Jan. 26, 1993: 19-35.
Hetzer R. et al., 1998, Daily non-invasive rejection monitoring improves long-term survival in pediatric heart transplantation, Ann. Thorac. Surg. (66):1343-1349.
J.A. Parrish, "Photobiologic Consideration on Photoradiation Therapy," pp. 91-108, Porphyrin Photosensitization, Plenum Press, (1983).
K.E. Uhrich et al., "Synthesis and characterization of degradable poly(anhydride-co-imides)", Macromolecules, 1995, 28, 2184-93.
Karl E. Richard et al. (Germany, Jan. 1999) "First clinical results with a telemetric shunt-integrated ICP-sensor" Neurological Research vol. 21, pp. 117-120.

Labrousse and Satre, "Photodynamic Killing of Dictyostelium Discoideum Amoebae Mediated by 4',5'-Diiodofluorescin Isothiocyanate Dextran. A strategy for the isolation of Thermoconditional Endocytosis Mutants," published in Photochemistry and Photobiology, 1993, vol. 67, No. 3, pp. 531-537.
Mackay et al., "Bio-medical Telemetry: Sensing and Transmitting Biological Information from Animals and Man," John Wiley & Sons, Inc. New York (1970) pp. 244-245.
Pfitzmann R, Muller J, Grauhan O. Cohnert T, Hetzer R, Z Kardiol, 1998, Measuring bioelectric myocardial impedance as a non invasive method for diagnosis of graft rejection after heart transplantation, 87(4):258-266.
Pirolo J S, Shuman T S, Brunt E M, Liptay M J, Cox J L, Ferguson T B Jr., J Thoracic Cardiovasc Surg, 1992, Noninvasive detection of cardiac allograft rejection by prospective telemetric monitoring, 103(5):969-79.
Prof. Dr. Johannes Zacheja et al. (Germany, Sep. 1996) "An Implantable Microsystem for Biomedical Applications" Micro System Technologies 96, pp. 717-722.
Rozenman, Yoseph et al., "Wireless Acoustic Communication With a Miniature Pressure Sensor in the Pulmonary Artery for Disease Surveillance and Therapy of Patients With Congestive Heart Failure", Journal of the American College of Cardiology, 49:7, 2007, pp. 784-789.
S.K. Gupta et al. (1999) "Use of a Piezoelectric Film Sensor for Monitoring Vascular Grafts", The American Journal of Surgery, vol. 160, pp. 182-186.
Strickberger, S. Adam et al., "Extracardiac Ablation of the Canine Atrioventricular Junction by Use of High-Intensity Focused Ultrasound", Circulation, Jul. 13, 1999; downloaded from circ.ahajournals.org at ACS/GUIDANT on Jan. 4, 2008, pp. 203-208.
T. Chuter et al. (Sweden, Jan. 1997) "Aneurysm Pressure Following Endovascular Exclusion" Eur. J. Vasc. Endovasc. Surg. vol. 13, pp. 85-87.
T.A. Cochran et al. (1990) "Aortic Aneurysm Abdominal", Current Therapy in Adult Medicine, Fourth Edition.
Wesseling, KH et al., "Computation of Aortic Flow From Pressure in Humans Using a Nonlinear, Three-Element Model", Journal of Applied Physiology, vol. 74, Issue 5, pp. 2566-2573 (1993.
Wu, Francois et al., "Time Reversal of Ultrasonic Fields—Part II: Experimental Results", IEEE Transactions on Ultrasonics, Ferroelectrics, and Frequency Control, vol. 39, No. 5, Sep. 1992, pp. 567-578.
Z. Tang et al. (May 1995) "Data Transmission from an Implantable Biotelemeter by Load-Shift Keying Using Circuit Configuration Modulator" IEEE Transactions on Biomedical Engineering. vol. 42, No. 5, pp. 524-528.
Cohen, T.J. et al., "A Hemodynamically Responsive Antitachycardia System. Development and Basis for Design in Humans", Circulation 1990, vol. 82, No. 2, pp. 394-406, XP002560584.
Blacher, Jacques et al., "Aortic Pulse Wave Velocity as a Member of Cardiovascular Risk in Hypertensive Patients", Hypertension May 1999;33;1111-1117.
Farzaneh-Far, Ramin et al., Usefulness of Noninvasive Estimate of Pulmonary Vascular Resistance to predict Mortality, Heart Failure, and Adverse Cardiovascular Events in Patients With Stable Coronary Artery Disease (from the Heart and Soul Study), The American Journal of Cardiology, vol. 101, Issue 6, Mar. 15, 2008, pp. 762-766.
El Gamal, M.I.H. et al., "Chronic Ventricular Pacing With Ventriculo-Atrial Conduction Versus Atrial Pacing in Three Patients With Symptomatic Sinus Bradycardia", PACE, vol. 4, Jan.-Feb. 1981, pp. 100-106.
Fujiki, Akira et al., "Pacemaker Syndrome Evaluated by Cardiopulmonary Exercise Testing", PACE, vol. 13, Oct. 1990, pp. 1236-1241.
International Search Report and Written Opinion issued in PCT/US2009/056549, mailed Dec. 4, 2009, 14 pages.
Garg et al., "Jugular Venous Pulse: An Appraisal", Journal, Indian Academy of Clinical Medicine, vol. 1, No. 3, Oct.-Dec. 2000, pp. 260-269.

* cited by examiner

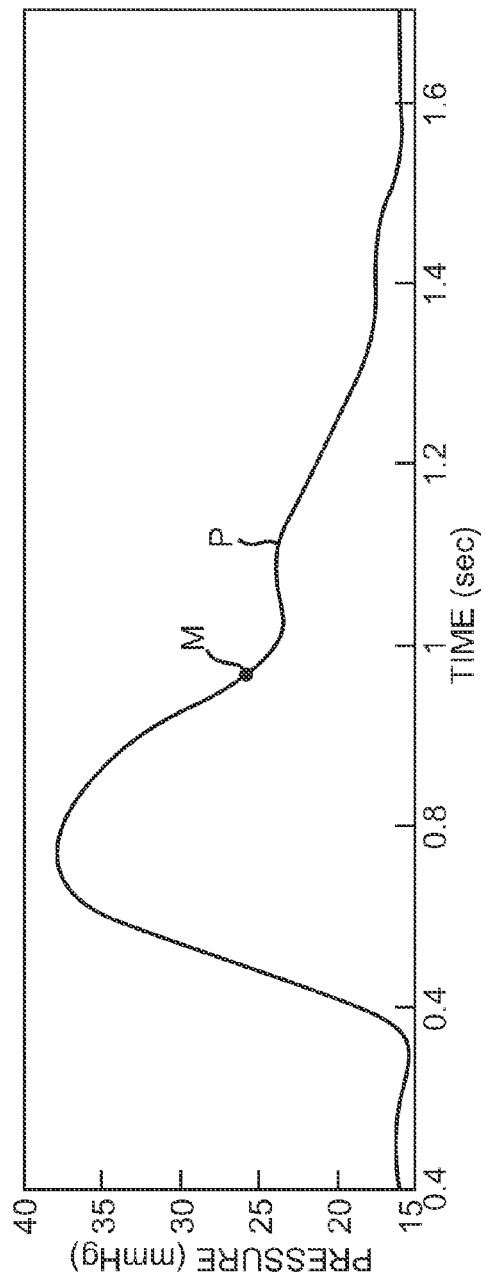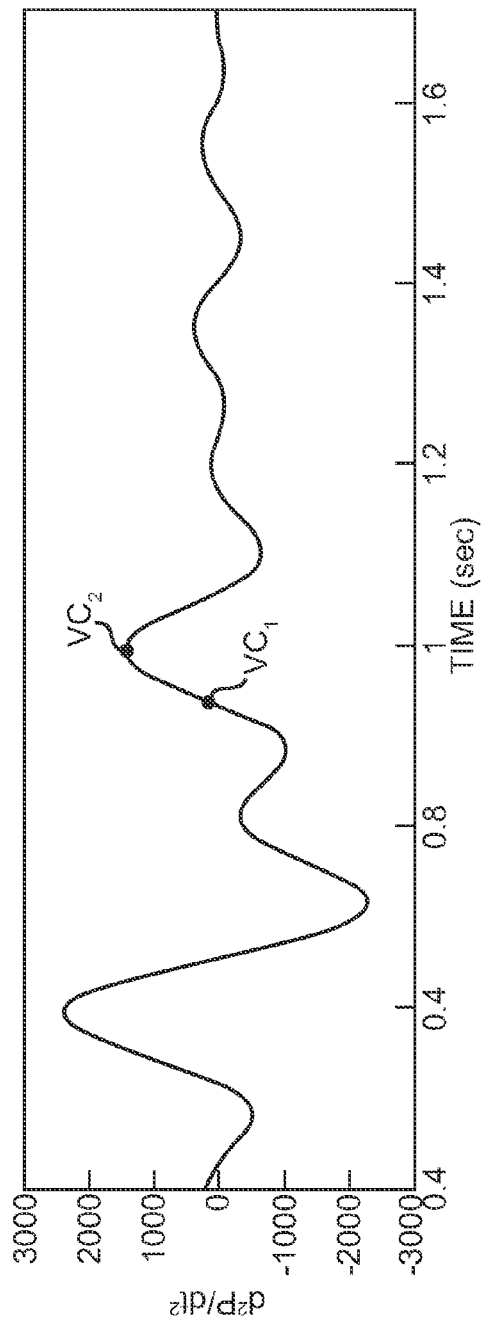

US 8,591,423 B2

SYSTEMS AND METHODS FOR DETERMINING CARDIAC OUTPUT USING PULMONARY ARTERY PRESSURE MEASUREMENTS

CROSS-REFERENCE TO RELATED APPLICATION

This application claims priority under 35 U.S.C. §119 to U.S. Provisional Application No. 61/104,405, filed on Oct. 10, 2008, entitled "Systems and Methods For Determining Cardiac Output Using Pulmonary Artery Pressure Measurements," which is incorporated herein by reference in its entirety for all purposes.

TECHNICAL FIELD

The present invention relates generally to systems and methods for measuring hemodynamic parameters within a patient. More specifically, the present invention pertains to systems and methods for determining cardiac output using pulmonary artery pressure measurements.

BACKGROUND

Cardiac output (CO) is defined generally as the volume of blood pumped through the heart per unit time, and is an important factor in monitoring the output of blood in heart failure patients. In intensive care units and surgical sites, for example, cardiac output is sometimes used in conjunction with other hemodynamic parameters to monitor the state of the patient's heart and circulatory system both during and after surgery. In surgical procedures where coronary artery bypass grafting or heart valve replacement is to be performed, for example, hemodynamic parameters such as stroke volume, heart rate, and cardiac output are sometimes used to assess heart performance both during and after the procedure. The monitoring of hemodynamic parameters can also be used for optimizing therapy provided to the patient via a pacemaker or cardiac defibrillator, and in detecting and assessing long term heart disease in certain, at-risk individuals. In some cases, hemodynamic parameters such as cardiac output can also be used to determine if a patient is dehydrating as a consequence of too many diuretics.

A variety of different techniques have been developed for measuring cardiac output within a patient. In one technique known as the Fick method, a measurement of the concentration of oxygen in the pulmonary artery, a peripheral artery, as well as respiratory oxygen are used to estimate cardiac output of the heart. In another technique, cardiac output is estimated using Doppler or duplex ultrasound techniques by measuring the flow velocity and the dimensions across the aortic and/or pulmonic annulus, or alternatively, across the aorta. The flow profile from these measurements provides the stroke volume, which is then multiplied by the heart rate in order to determine cardiac output. In yet another technique, a measurement procedure performed during catheterization uses thermodilution to estimate cardiac output by injecting a bolus of cold saline solution into the right ventricle, and then measuring the resulting temperature curve as the solution flows through the main pulmonary artery.

A number of different pulsed pressure (PP) algorithms have also been employed to estimate cardiac output by analyzing the shape of the blood pressure waveform at a given location within the body. In some systems, for example, a catheter or other device may be positioned at a location within the body such as the aorta or left radial artery for sensing physiological parameters such as blood pressure. These systems typically analyze only the left side, or systemic blood pressure, however, which are typically more accessible for acute or semi-acute applications. Left-side pulsed pressure algorithms used for estimating cardiac output are not directly applicable to right side pressure waveforms, and are therefore often ineffective in extracting many hemodynamic parameters. For example, the diastolic waveform derived using right side pressure measurements does not behave as a decaying exponential, and is instead dominated by wave reflections and artifacts. As a result, it is often difficult to extract vascular parameters employed in pulsed pressure algorithms for computing hemodynamic parameters such as cardiac output from right-side pressure waveforms.

SUMMARY

The present invention pertains to system and methods for determining cardiac output using pulmonary artery pressure measurements. An illustrative system for determining cardiac output includes a pressure sensor located within a pulmonary artery of the patient. The pressure sensor is adapted to sense arterial blood pressure within the pulmonary artery and transmit a pressure waveform signal to another device located inside or outside of the patient's body. The communicating device can include a processor adapted to run an algorithm or routine that determines a measure of cardiac output based at least in part on the pressure waveform signal transmitted by the pressure sensor. In some embodiments, the processor is adapted to determine cardiac output based on a valve closure time associated with the pulmonary heart valve and the systolic portion of the sensed arterial pressure waveform.

An illustrative method of determining cardiac output includes sensing an arterial pressure waveform using a pressure sensor located within a pulmonary artery of the patient, identifying the beginning of a cardiac cycle and correlating the arterial pressure waveform with the beginning of the cardiac cycle, identifying a value of the valve closure time associated within the pulmonary valve based on the sensed arterial pressure waveform, estimating the stroke volume based on the sensed arterial pressure waveform and the valve closure time, and obtaining a measure of cardiac output from the estimated stroke volume.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 4A and 4B are several graphs showing the determination of the valve closure time from an arterial pressure waveform over a single heartbeat.

Figure 1:
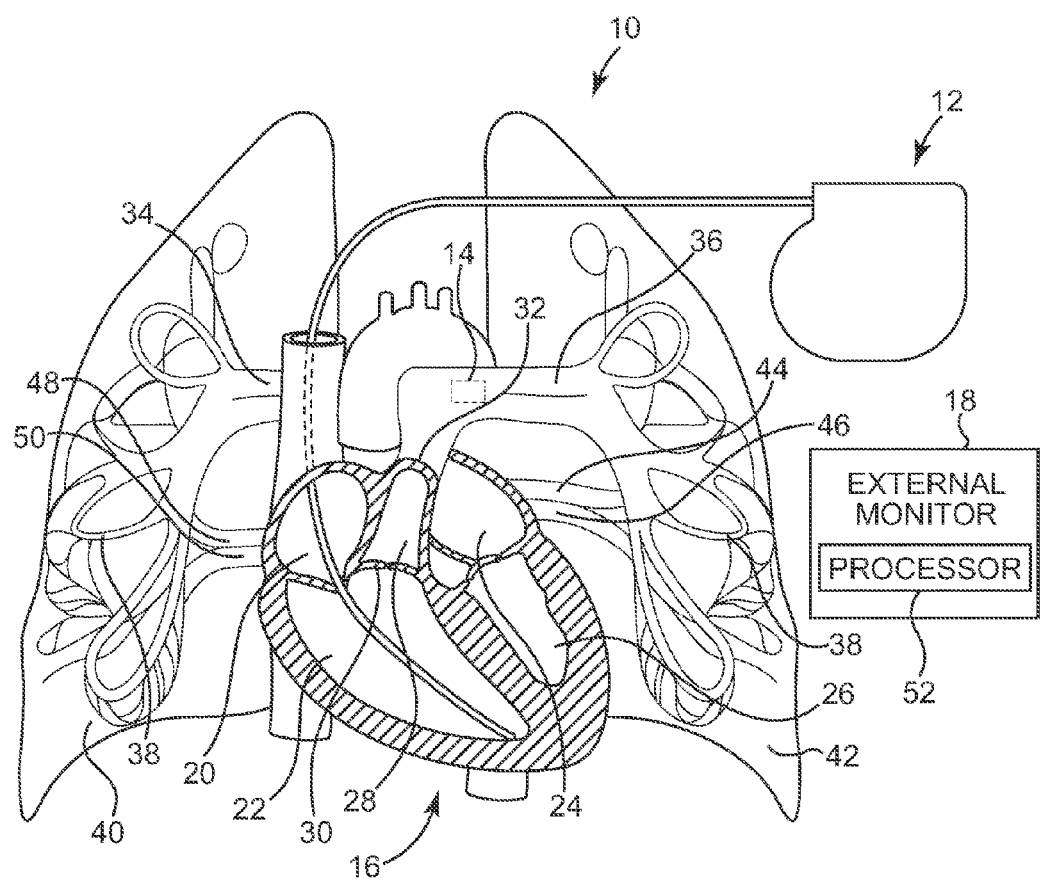
FIG. 1 is a schematic view showing an illustrative system for determining cardiac output within a patient's heart using pulmonary artery pressure measurements.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view showing an illustrative system 10 for determining cardiac output using pulmonary artery pressure measurements. In the embodiment of FIG. 1, the system 10 includes a pulse generator 12 implanted within the body at a location below the patient's skin, a remote pressure sensor 14 implanted deeply within the patient's body such as in one of the pulmonary arteries leading from the patient's heart 16, and an external monitor 18 positioned at a location outside of the patient's body.

The heart 16 includes a right atrium 20, a right ventricle 22, a left atrium 24, and a left ventricle 26. The right ventricle 22 includes an outflow tract 28 that leads to the pulmonary valve 30, which opens during ventricular systole to deliver blood through the main pulmonary artery 32. When this occurs, the contraction of the myocardial muscles in the heart 16 discharges blood into the right pulmonary artery 34 and the left pulmonary artery 36, which, in turn, flows into the capillaries 38 of the lungs 40,42 and returns back to the heart 16 via the pulmonary veins 44,46,48,50. At the end of ventricular systole, when the pressure in the right ventricle 22 falls rapidly, the pressure in the pulmonary artery 32 causes the pulmonary valve 30 to close. The point at which the blood flow across the pulmonary valve 30 stops and the valve 30 starts to close is often referred to as the dicrotic notch, and represents the period at which no pressure drop occurs across the valve 30.

The remote pressure sensor 14 can be implanted at a location such as the main pulmonary artery 32 or a branch of the main pulmonary artery such as the right or left pulmonary artery 34,36. An illustrative pressure sensor suitable for use in sensing arterial pressure within the body is described, for example, in U.S. Pat. No. 6,764,446, entitled "Implantable Pressure Sensors and Methods for Making and Using Them," the contents of which are incorporated herein by reference in its entirety.

Although the embodiment of FIG. 1 illustrates a remote pressure sensor that can be implanted within the body, in other embodiments the pressure sensor may comprise an acute or semi-acute sensing device that can be temporarily inserted into the patient's body for sensing arterial pressure. In one alternative embodiment, for example, the pressure sensor 14 can be coupled to or formed integrally with a catheter that can be temporarily inserted into the body for sensing blood pressure within a pulmonary artery. Other devices that are temporarily or permanently insertable within the body can also be used for obtaining blood pressure measurements within a pulmonary artery.

The pressure sensor 14 can be implanted at other locations such as the right ventricle 26 of the heart 16, and can be configured to perform one or more other designated functions, including the sensing of other physiological parameters within the body. Example physiological parameters that can also be sensed using the pressure sensor 14 can include, but are not limited to, blood flow, temperature, strain, acceleration, as well as various electrical, chemical and/or magnetic properties within the body.

The pressure sensor 14 can be used in conjunction with the pulse generator 12 and/or the external monitor 18 to optimize pacing and/or defibrillation therapy, to predict decompensation of a heart failure patient, or to provide other monitoring and/or therapy functions. In certain embodiments, for example, the pressure sensor 14 can be utilized in conjunction with the pulse generator 12 to provide cardiac defibrillation or pacing to the patient based at least in part on a measure of cardiac output from the heart 16. Other devices such as a pulmonary sound sensor, satellite pacing device, or other sensing and/or therapy-delivering device may also be used in conjunction with the pulse generator 12 and pressure sensor 14.

The pressure sensor 14 can be configured to communicate with the pulse generator 12 and/or the external monitor 18 via a wireless or wired telemetry link. In some embodiments, for example, an acoustic telemetry link may be used to establish bidirectional wireless communications between the pressure sensor 14 and the pulse generator 12, and/or between the pressure sensor 14 and the external monitor 18. An example wireless telemetry system employing acoustic transducers is described, for example, in U.S. Pat. No. 7,024,248, entitled "Systems and Methods For Communicating With Implantable Devices," the contents of which are incorporated herein by reference in its entirety. Other types of telemetry modes such as RF, inductive, electromagnetic, and optical may also be utilized to establish a wireless telemetry link between the pressure sensor 14 and the pulse generator 12 and/or external monitor 18. In some embodiments, the pressure sensor 14 can communicate with other devices implanted within the body via either a wireless or wired telemetry link.

The external monitor 18 is configured to monitor an arterial pressure waveform signal transmitted by the pressure sensor 14. Based on this signal, a processor 52 within the external monitor 18 is configured to determine various hemodynamic parameters associated with the heart 16, including, but not limited to, stroke volume, heart rate, the pulmonary time constant $\tau$, and cardiac output. In some embodiments, other hemodynamic parameters such as pulmonary vascular resistance (PVR) can also be determined from the arterial pressure waveform sensed by the pressure sensor 14. As discussed further herein, these parameters can be determined from an analysis of the right side pressure, and in particular, based on an analysis of the systolic portion of the arterial pressure waveform sensed by the pressure sensor 14.

Although an external monitor 18 is used in the illustrative system 10 of FIG. 1 for determining hemodynamic parameters such as cardiac output, in other embodiments other devices can be configured to compute one or more hemodynamic parameters based on the arterial pressure waveform sensed by the pressure sensor 14. In one alternative embodiment, for example, the pulse generator 12 includes a processor adapted to compute hemodynamic parameters based at least in part on the arterial pressure waveform signal from the pressure sensor 14. In another alternative embodiment, the pressure sensor 14 includes a processor adapted to compute hemodynamic parameters based at least in part on the sensed arterial pressure waveform signal.

The vascular system can be modeled as an equivalent electrical circuit, which as discussed further herein, can be used by the processor 52 to perform an analysis of the right side arterial pressure waveform signal transmitted by the pressure sensor 14. In some embodiments, an analysis of only the systolic portion of the arterial pressure waveform signal is used to determine cardiac output. The ability to directly determine cardiac output using the systolic portion of the pressure waveform overcomes some of the problems associated with continuous cardiac output measurement algorithms that employ left side algorithms, which are not directly applicable to right side pressure waveforms. This is due primarily to the fact that the time constant $\tau$, which describes the speed at which the vascular blood pressure relaxes during diastole, is much smaller on the right side of the heart 16 than on the left side as a result of the smaller extent of the great vessels (e.g., the pulmonary arteries) on the right side of the heart 16 versus the vessels on the left side of the heart 16 (e.g., the ascending, descending and thoracic aorta, the iliac and femoral arteries, the radial arteries, etc.). The diastolic waveform relied upon by some techniques for computing cardiac output, therefore, does not behave as a decaying exponential, but is instead dominated by wave reflections and artifacts, making it difficult to extract vascular parameters such as the time constant τ often used by pulsed pressure (PP) algorithms in computing cardiac output.

Figure 2:
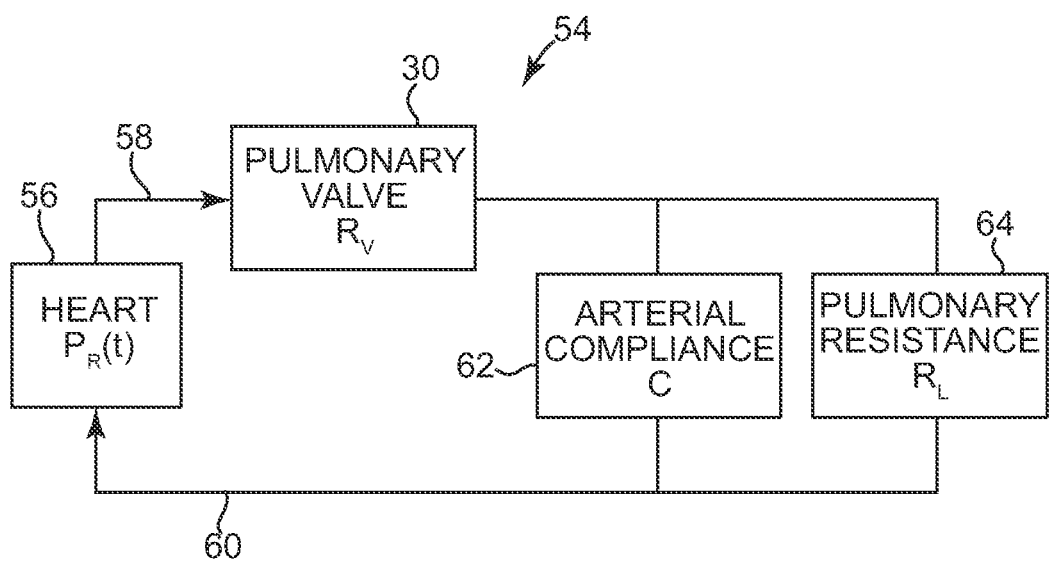
FIG. 2 is a block diagram showing an equivalent electrical circuit for modeling the vascular system of a patient.

FIG. 2 is a block diagram showing an illustrative equivalent electrical circuit 54 for modeling the vascular system of a patient. The equivalent electrical circuit 54 may represent, for example, several analogous electrical elements that can be used to model the mechanical operation of the heart 16, including the mechanical properties of the right ventricle, the pulmonary valve, the pulmonary vasculature, and the lung vasculature. As shown in FIG. 2, a pressure waveform 56 is represented generally in the electrical circuit 54 as $P_R(t)$. In some embodiments, for example, the output 58 of the pressure waveform 56 may comprise an arterial pressure waveform signal obtained from a remote pressure sensor 14 implanted within the right pulmonary artery 34, the left pulmonary artery 36, or the main pulmonary artery 32. A reference pressure 60 in the electrical circuit 54, in turn, may represent the left atrial filling pressure of the heart 16.

The arterial compliance 62 for the arterial tree may be represented generally in the electrical circuit 54 as a capacitance C. The arterial compliance 62 may represent, for example, a measure of the change in volume or stretching of the pulmonary artery in response to a change in arterial blood pressure. The pulmonary artery increases in diameter when the blood pressure rises during systole and decreases in diameter as the blood pressure falls during diastole.

The mechanical resistance 64 to the blood flow within the arterial tree may be represented generally as $R_L$, which is shown in the electrical circuit 54 as a resistor in parallel with the arterial compliance 62 (i.e., capacitance C) of the circuit 54. The mechanical resistance 64 may represent, for instance, the pulmonary vascular resistance (PVR) in the lung vasculature. The mechanical resistance of the pulmonary valve 30, in turn, may be modeled as a series resistance $R_V$ in the electrical circuit 54.

The electrical circuit 54 depicted in FIG. 2 may be based on several assumptions that can be used to simplify the mechanical to electrical relationship of the heart 16 and the arterial tree. For example, the various electrical components, including the arterial compliance C and the pulmonary resistance $R_L$, can be modeled as linear elements such that the equivalent impedance of these elements is not affected by the blood pressure. This assumption is justified since the pressures in the right side of the heart 16 are typically much lower than that of the left side of the heart 16. In addition, the equivalent electrical circuit 54 assumes that the pulmonary valve resistance $R_V$ is relatively small, which occurs when the pulmonary valve 30 is not occluded. The electrical circuit 54 further assumes that there is no backflow through the pulmonary valve 30, and that there is negligible mitral regurgitation.

The relationship between the pressure and the flow across each of the elements can be described as a set of equations analogous to Ohm's law equations. The volumetric flow, which is analogous to an electric charge, can be denoted as Q and its time derivative is the volumetric flow velocity. From this, the following set of expressions can be obtained:

Pressure drop across the value: $P_A - P_R = \dot{Q}R_V$;  (1)

Excess volume in the arteries: $Q_A = CP_A$;  (2)

Flow across the lungs: $P_A = \dot{Q}_L R_L$;  (3)

Continuity equation: $Q = Q_A + Q_L$; and  (4)

Connection to the vascular pressure: $P_R = \dot{Q}R_V + \frac{Q_A}{C}$;  (5)

where $P_A$ is the pressure across the lungs 40,42, and $P_R$ is the right ventricular pressure.

The pressure $P_A$ in the above expressions (1) to (5) can be defined generally as the pressure measured at various locations (i.e., the pressure at the output 58 in the electrical circuit 54) subtracted by the pressure on the other side of the lungs 40,42 (i.e., the left atrial filling pressure 60 in the electrical circuit 54). All of the above expressions (1) to (5) can be combined together and expressed as the following differential equation:

$$0 = R_V C \dot{Q}_A + Q_A\left(\frac{R_V}{R_L} + 1\right) - CP_R. \quad (6)$$

In the above equation (6), the flow $Q_A$ is to leading order independent of $R_V$, for sufficiently low values of $R_V$. This is based on the assumption that, for sufficiently small pulmonary valve resistances $R_V$ relative to other values (e.g., pulmonary resistance $R_L$), the valve resistance $R_V \ll R_L$ and thus does not significantly affect the result. Based on the relatively small value of $R_V$, the above equation (6) can thus be solved by expanding the solution in terms of the powers in the expression $R_V/R_L$, as follows:

$$Q_A = Q_A^{(0)} + \frac{R_V}{R_L}Q_A^{(1)} + O\left(\frac{R_V^2}{R_L^2}\right). \quad (7)$$

Substitution and solving each of the above powers separately yields the following expression to first order:

$$P_A = \frac{Q_A}{C} = \left(1 - \frac{R_V}{R_L}\right)P_R - R_V C \dot{P}_R. \quad (8)$$

As discussed previously, the dicrotic notch represents the point at which the flow across the pulmonary valve 30 stops and the valve 30 begins to close. According to some embodiments, for example, the dicrotic notch can be measured from the systole portion of the right side arterial pressure waveform obtained from the pressure sensor 14. At the dicrotic notch, $P_R = P_A$, and thus the above expression (8) yields:

$$0 = P_R + R_L C \dot{P}_R \Rightarrow \tau \equiv R_L C = -\frac{P_R(t_{notch})}{\dot{P}_R(t_{notch})} \quad (9)$$

where $t_{notch}$ is the time at which the dicrotic notch occurs, and τ is the time constant representing the speed at which the pulmonary artery blood pressure relaxes during diastole.

The above expression (9) thus permits an estimation of the stroke volume of the heart 16 using only the systolic portion of the arterial pressure waveform sensed by the pressure sensor 14. This is due in part since during systole, when the pulmonary valve 30 is open, the ventricular pressure $P_R$ is similar or equal to the pulmonary artery pressure $P_A$. From this, the stoke volume can thus be obtained based on the following equation:

$$V_{stroke} = C\tau \int_{t_0}^{t_{notch}} P_A(t)\,dt + CP_A(t_{notch}); \qquad (10)$$

where $t_0$ signifies the beginning of the cardiac cycle. The cardiac output can then be obtained by multiplying the above-computed value for the stroke volume ($V_{stroke}$) by the patient's heart rate.

Figure 3:
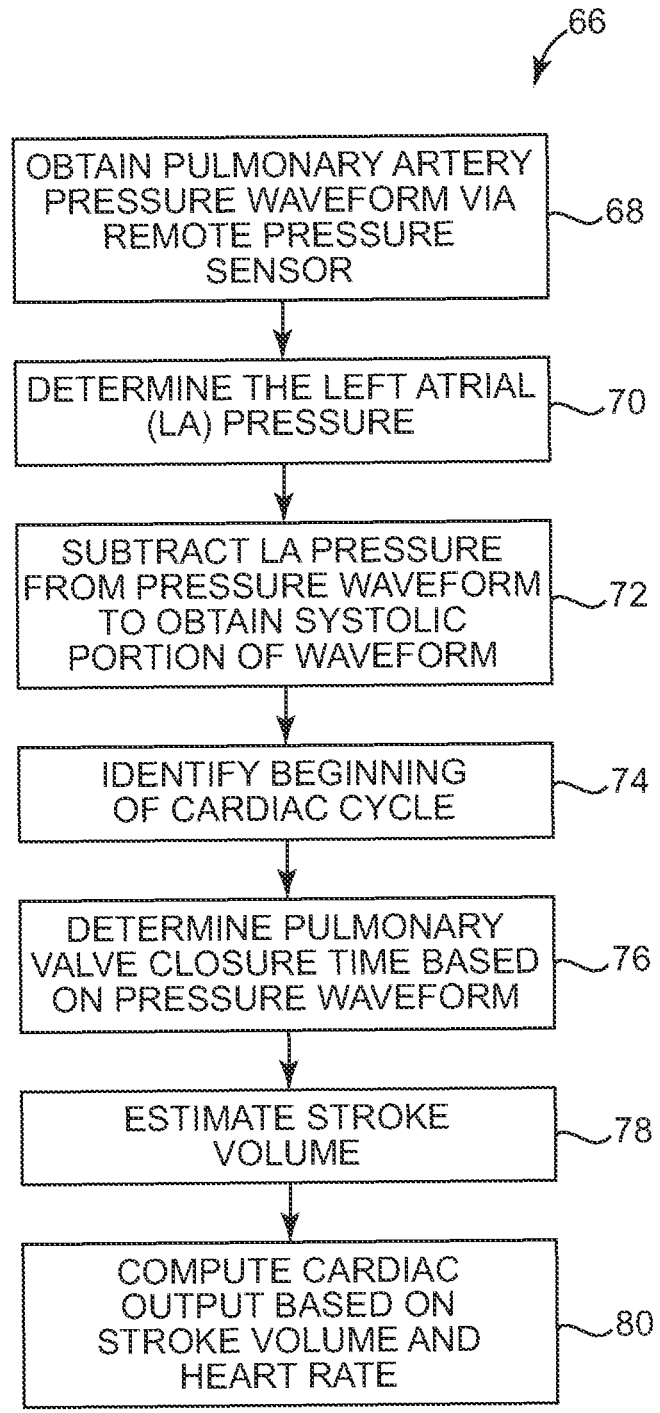
FIG. 3 is a flow chart showing an illustrative method of determining cardiac output using pulmonary artery pressure measurements.

FIG. 3 is a flow chart showing an illustrative method 66 of determining cardiac output using pulmonary artery pressure measurements. Method 66 may represent, for example, an algorithm or routine used by the external monitor processor 52 of FIG. 1 to compute a measure of cardiac output based on an arterial pressure waveform signal transmitted by the pressure sensor 14. Alternatively, and in other embodiments, the method 66 may represent an algorithm or routine run by another device located inside or outside of the patient's body. In one alternative embodiment, for example, the method 66 may be performed by the pulse generator 12, another implant located within the body, or by the pressure sensor 14.

In the embodiment of FIG. 3, the method 66 may begin generally at block 68 with the step of obtaining a pulmonary artery pressure waveform from a pressure sensor located within a pulmonary artery. In certain embodiments, for example, the pulmonary artery pressure waveform may be obtained via a pressure sensor 14 implanted within the left pulmonary artery 36, as shown in FIG. 1. Alternatively, and in other embodiments, a measure of the pulmonary artery pressure waveform can be obtained by taking pressure measurements at other locations within the arterial tree such as in the right pulmonary artery 34, or in the main pulmonary artery 32, or by taking pressure measurements in the right ventricle 22.

From the arterial pressure waveform sensed by the pressure sensor 14, the processor 52 can then be configured to determine the left atrial filling pressure ($P_A$) within the heart 16 (block 70). In some embodiments, the left atrial filling pressure can be estimated from the diastolic pulmonary artery pressure. Other means for estimating the left atrial filling pressure can also be used. The estimated left atrial filling pressure can then be subtracted from the pulmonary artery pressure waveform sensed by the pressure sensor 14 in order to obtain the systolic portion of the arterial pressure waveform (block 72).

The beginning of the cardiac cycle is then identified (block 74) and correlated with the systolic portion of the arterial pressure waveform. Identification of the beginning of the cardiac cycle can be accomplished, for example, by identifying a sudden, fast rise in pulmonary artery pressure detected by the pressure sensor 14. Alternatively, the identification of the beginning of the cardiac cycle can be obtained from other, external factors. Example external factors that can be used to identify the beginning of the cardiac cycle can include, for example, the detection of electrical ECG signals from an electrode coupled to the heart 16 and/or from the detection of an acceleration of the heart 16 via an accelerometer. Other techniques for identifying the beginning of the cardiac cycle can also be used. In one alternative embodiment, for example, the beginning of the cardiac cycle can be determined by sensing heart sounds using an acoustic sensor.

Based on the beginning of the cardiac cycle, an evaluation of the valve closure time ($t_{notch}$) at which the dicrotic notch occurs can then be made based on the arterial pressure waveform sensed by the pressure sensor 14 (block 76). The valve closure time ($t_{notch}$) at which the dicrotic notch occurs is immediately before the actual closure of the pulmonary valve 30 since the valve 30 requires at least some backflow in order to fully close. In some embodiments, the valve closure time ($t_{notch}$) can be approximated based on several points on the arterial pressure waveform, as correlated with the cardiac cycle. In some embodiments, for example, the valve closure time ($t_{notch}$) can be determined by finding a first point corresponding to the point of maximum pressure velocity, or equivalently, the positive-going zero of the second derivative, which signifies the point at which the pulmonary pressure drop, resulting from ventricular relaxation, starts to slow down or decelerate. At this point, the valve is starting to close. The valve closure time ($t_{notch}$) can be further approximated from a second point corresponding to the maximum positive value of the second derivative of the pressure waveform, once the valve has already closed. This second point may be either an inflection point or a minimum of the pulmonary pressure, and signifies the point where the slowing pressure drop due to the valve closure is offset by an increasing pressure drop due to vascular, rather than ventricular, relaxation.

FIGS. 4A-4B are several graphs showing the determination of the valve closure time ($t_{notch}$) from an arterial pressure waveform P over a single heartbeat. As shown in FIG. 4B, which represents the second derivative ($d^2P/dt^2$) of an arterial pressure waveform P depicted in FIG. 4A, the point at which the pulmonary valve 30 begins to close can be seen at $VC_1$ whereas the point $VC_2$ at which the valve 30 is closed can be seen at $VC_2$. Point $VC_1$ can be determined, for example, by sensing the point where the pulmonary pressure drop starts to decelerate due to the beginning of the pulmonary valve closure. Point $VC_2$, in turn, can be determined by sensing the subsequent maximum of the second derivative of the pressure waveform P, which signifies the point at which the valve has fully closed. As shown in FIG. 4A, the midpoint M in time between points $VC_1$ and $VC_2$ in the pressure waveform P represents the equalization point of the valve closure, which provides an estimate of the valve closure time ($t_{notch}$).

From the determination of the valve closure time ($t_{notch}$) (block 76), and as further shown in FIG. 3, a measure of the stroke volume ($V_{stroke}$) is then computed (block 78). In some embodiments, for example, the stroke volume ($V_{stroke}$) can be determined from equation (10) discussed above, using only the arterial pressure waveform values $P_A(t)$ obtained from the pressure sensor 14 and the value of the arterial compliance C. Since the arterial compliance C is not anticipated to change rapidly, but instead gradually changes over the life of the patient, the value of the compliance C can be obtained from a previous calibration step. Alternatively, and in other embodiments, the arterial compliance C can be estimated using a model of the arterial tree, or can be provided to the processor 52 as a value contained, for example, in a look-up table.

In one embodiment, the arterial compliance C can be calibrated by directly measuring the cardiac output in a separate step using a thermodilution catheter during an invasive procedure, or alternatively, using the Fick method. Simultaneously, a measure of the pulmonary artery or right ventricular pressure can be obtained, either via the pressure sensor 14 or from another device located within the body. From this separate cardiac output measurement and the pressure measurement(s), a calibrated value of the compliance C can then be obtained by comparing these signals against the actual compliance values obtained using the pulmonary artery pressure method 66 disclosed herein. This calibration process can then be repeated one or more times to smooth out the presence of any noise.

The time constant (τ) obtained from the valve closure time $t_{notch}$ can be acquired over a single cardiac cycle (i.e., beat to beat), or across several cardiac cycles. In those patients where the method 66 may be prone to errors due to irregular heartbeats and pressure waveforms, for example, the system may evaluate an averaged time constant by evaluating τ over several cycles. For example, and in some embodiments, the method 66 may replace the beat to beat value of τ by an average or median value measured over a longer period of time.

Once the stroke volume ($V_{stroke}$) is determined (block 78), a measure of the cardiac output can then be obtained by multiplying the stroke volume by the heart rate (block 80). The heart rate can be determined, for example, from an analysis of the arterial pressure waveform sensed by the pressure sensor 14, or alternatively from another source such as an external heart rate monitor (e.g., via the external monitor 18). If desired, the method 66 may then be repeated for multiple cardiac cycles in order to obtain an average or median value of the cardiac output over time.

The systems and methods discussed herein can be used to determine other hemodynamic parameters in addition to, or in lieu of, cardiac output. In one alternative embodiment, for example, the method may be used to evaluate the pulmonary time constant $\tau = R_L C$, which may be useful in evaluating the pulmonary vascular resistance ($R_L$). For instance, the pulmonary vascular resistance may be useful in diagnosing cases of pulmonary hypertension, either primary or secondary, as a side effect of heart failure. Using the valve closing time $t_{notch}$, the pulmonary vascular resistance $R_L$ can be evaluated based on the following equation:

$$R_L = \frac{\tau}{C} = -\frac{P_A(t_{notch})}{C\dot{P}_A(t_{notch})}. \quad (11)$$

If the arterial compliance C is known, the above equation (11) can be used to obtain an absolute measurement of the pulmonary vascular resistance. Otherwise, if the arterial compliance C is unknown, the method may be used to track changes in the pulmonary vascular resistance ($R_L$) over time, response to medication, response to therapy, or other variables of interest.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method of determining cardiac output within a patient's heart, the method comprising:

sensing an arterial pressure waveform using a pressure sensor located within a pulmonary artery of the patient in order to sense the arterial pressure waveform on a right side of the patient's heart;

identifying the systolic portion of the arterial pressure waveform sensed by the pressure sensor;

identifying the beginning of a cardiac cycle and correlating the systolic portion of the arterial pressure waveform with the beginning of the cardiac cycle;

identifying an estimate of the valve closure time of the pulmonary valve using the arterial pressure waveform, wherein identifying the estimate of the valve closure time of the pulmonary valve includes:

determining a first point, the first point comprising a positive-going zero of a second derivative of the arterial pressure waveform;

determining a second point, the second point comprising a point of maximum positive value of the second derivative of the arterial pressure waveform; and determining a midpoint in time between the first point and the second point, wherein the midpoint provides the estimate of the valve closure time of the pulmonary valve;

estimating the stroke volume using the systolic portion of the arterial pressure waveform and the estimate of the pulmonary valve closure time; and obtaining a measure of cardiac output based at least in part on the estimated stroke volume.

2. The method of claim 1, further including determining the left atrial filling pressure within the heart based on an estimate of diastolic pulmonary artery pressure from the arterial pressure waveform.

3. The method of claim 2, wherein identifying the systolic portion of the arterial pressure waveform includes subtracting the left atrial filling pressure from the arterial pressure waveform.

4. The method of claim 1, wherein identifying the beginning of a cardiac cycle includes identifying an increase in blood pressure from the arterial pressure waveform.

5. The method of claim 1, wherein identifying the beginning of a cardiac cycle includes sensing an ECG signal associated with the heart.

6. The method of claim 1, wherein identifying the beginning of a cardiac cycle includes sensing an acceleration associated with the heart.

7. The method of claim 1, wherein estimating the stroke volume is based at least in part on a measure of arterial compliance.

8. The method of claim 1, wherein obtaining a measure of the cardiac output based at least in part on the estimated stroke volume includes sensing a heart rate associated with the heart, and multiplying the sensed heart rate by the stroke volume.

9. The method of claim 1, wherein the method comprises an algorithm or routine operable on an implantable device or an external device in communication with the pressure sensor.

10. The method of claim 1, wherein the method comprises an algorithm or routine operable within a processor of the pressure sensor.

11. The method of claim 1, further comprising evaluating one or more additional hemodynamic parameters.

12. The method of claim 11, wherein the one or more additional hemodynamic parameters includes a measure of pulmonary vascular resistance.

13. A method of determining one or more hemodynamic parameters associated with the operation of a patient's heart, the method comprising:

sensing an arterial pressure waveform using a pressure sensor located within a pulmonary artery of the patient in order to sense the arterial pressure waveform on a right side of the patient's heart;

identifying the beginning of a cardiac cycle and correlating the arterial pressure waveform sensed by the pressure sensor with the beginning of the cardiac cycle;

identifying an estimate of the valve closure time of the pulmonary valve using the arterial pressure waveform, wherein identifying the estimate of the valve closure time of the pulmonary valve includes:

determining a first point, the first point comprising a positive-going zero of a second derivative of the arterial pressure waveform;

determining a second point, the second point comprising a point of maximum positive value of the second derivative of the arterial pressure waveform; and determining a midpoint in time between the first point and the second point, wherein the midpoint provides the estimate of the valve closure time of the pulmonary valve; and obtaining at least one hemodynamic parameter associated with the patient's heart based at least in part on the estimate of the valve closure time.

14. A system for determining cardiac output within a patient's heart, the system comprising:

a pressure sensor located within a pulmonary artery of the patient, the pressure sensor adapted to sense right side arterial blood pressure within the artery and transmit an arterial pressure waveform signal;

a monitoring device in communication with the pressure sensor, the monitoring device including a processor adapted to determine cardiac output based at least in part on the arterial pressure waveform signal; and wherein the processor is adapted to determine cardiac output based at least in part on a valve closure time associated with the pulmonary valve, wherein the processor is further adapted to determine an estimate of the valve closure time of the pulmonary valve by:

determining a first point, the first point comprising a positive-going zero of a second derivative of the arterial pressure waveform;

determining a second point, the second point comprising a point of maximum positive value of the second derivative of the arterial pressure waveform; and determining a midpoint in time between the first point and the second point, wherein the midpoint provides the estimate of the valve closure time of the pulmonary valve.

15. The system of claim 14, wherein the monitoring device comprises an external monitor.

16. The system of claim 14, wherein the monitoring device comprises an implantable medical device.

17. The system of claim 16, wherein the implantable medical device is a pulse generator.

18. The system of claim 14, wherein the pressure sensor is a remote pressure sensor adapted to wirelessly transmit the arterial pressure waveform signal to the monitoring device.

* * * * *